United States Patent
Viamonte, Jr.

(10) Patent No.: US 6,875,453 B2
(45) Date of Patent: Apr. 5, 2005

(54) NON-TOXIC DISINFECTANT CONTAINING A ISOPROPYL ALCOHOL AND SESAME OIL COMPOSITION WITH LEMON OIL AND MENTHOL

(76) Inventor: Manuel Viamonte, Jr., 1643 Brickell Ave., Apt. 2805, Miami, FL (US) 33129

( * ) Notice: Subject to any disclaimer, the term of this patent is extended or adjusted under 35 U.S.C. 154(b) by 0 days.

(21) Appl. No.: 10/815,779

(22) Filed: Apr. 2, 2004

(65) Prior Publication Data

US 2005/0013881 A1 Jan. 20, 2005

Related U.S. Application Data

(63) Continuation-in-part of application No. 10/622,977, filed on Jul. 18, 2003.

(51) Int. Cl.$^7$ ........................ A61K 35/78; A61K 31/045
(52) U.S. Cl. ........................ 424/736; 424/747; 424/776; 424/405; 514/724
(58) Field of Search ................................ 424/736, 747, 424/776, 405; 514/724

(56) References Cited

U.S. PATENT DOCUMENTS

| | | | | |
|---|---|---|---|---|
| 6,183,766 B1 | * | 2/2001 | Sine et al. | 424/405 |
| 6,294,186 B1 | * | 9/2001 | Beerse et al. | 424/405 |
| 6,296,882 B1 | * | 10/2001 | Viamonte, Jr. | 424/736 |
| 6,423,329 B1 | * | 7/2002 | Sine et al. | 424/405 |
| 6,436,885 B2 | * | 8/2002 | Biedermann et al. | 510/131 |

\* cited by examiner

*Primary Examiner*—Christopher R. Tate
(74) *Attorney, Agent, or Firm*—John S. Hale; Gipple & Hale

(57) ABSTRACT

A non-toxic mucosal disinfectant for topical application in the nose, skin, mouth and hard surfaces comprising a composition of 99.0% isopropyl alcohol of at least 24.0% by weight; sesame oil not exceeding 73.0% by weight and lemon oil of less than 3.0% by weight and menthol less than 1.0% by weight. All of the components are mixed homogenously with the sesame oil supplementing and neutralizing the dehydrating effect of the alcohol.

23 Claims, No Drawings

NON-TOXIC DISINFECTANT CONTAINING A ISOPROPYL ALCOHOL AND SESAME OIL COMPOSITION WITH LEMON OIL AND MENTHOL

RELATED CASES

This is a continuation-in-part application of U.S. patent application Ser. No. 10/622,977, filed Jul. 18, 2003.

FIELD OF THE INVENTION

The present invention is generally directed toward a topical disinfectant and more specifically is directed toward a non-toxic disinfectant effective against various pathogenic organisms which cause infectious processes.

DESCRIPTION OF THE PRIOR ART

Infectious diseases remain the leading cause of death. Even the domestication of animals has resulted in a number of illnesses (Diphtheria cam from the water buffalo; mycobacteria from ungulates; measles from canine distemper, etc.).

While some microorganisms are pathogens ( a microorganism capable of causing disease) most microorganisms that are seen in the human body are innocuous. For example, more than 600 species of bacteria inhabit the large bowel of a human; about 100 trillion microorganisms reside in the human body. Not only are the majority of human microorganisms innocuous but they play useful, if unseen roles. These microorganisms provide a necessary part of the development pathways required for the maturation of human intestinal mucosa and our innate local immune system protects us against harmful microorganisms and helps the digestion of food.

Most of human microbes are connected. Commensal or transient microbes can be an opportunistic pathogen of humans; namely, they can cause disease if one or more defense mechanisms are breached by accident, medical intent, or an underlying metabolic or even infectious disorder.

Many microorganisms are adapted exclusively to humans and other animals and many pathogenic microorganisms have learned to circumvent, exploit, subvert or avoid our normal cellular mechanisms to multiply at human expense. Some microbes have made the transition from harmless commensal to potentially fatal infectious agents.

Increases in the world population, rapid travel between distant regions, high concentration of individuals in small areas, the wide spread use of air conditioning and heating equipment without air exchange, the large number of people traveling in confined areas (i.e., aircraft, trains, subways, buses, and automobiles), have resulted in the increase in the number of pathogenic organisms and the increase of mutations of such organisms.

Thus, there is a need for effective protective measures to decrease the number and severity of respiratory infections. Some societies use face masks as a protecting against respiratory infections. However, the use of face masks are an impractical, inefficient and largely ineffective way to prevent dissemination of infection. The basic rules of hygiene are not practiced by most people on this planet.

There a number of highly contagious respiratory infections which result in fatal illness, such as African Ebola viruses. Some people have a decreased or defective immunological response to such infections. People who reside in high density cities are at risk for a large variety of respiratory illnesses. Many of the respiratory illnesses do not become confined to the respiratory tract (upper and/or lower) and can disseminate or other organs or become systematic infections.

It is estimated that an American catches an average of two to four colds a year. When symptoms first become noticeable there are thousands of viruses in the lung. As few as ten cold viruses may be enough to cause infection. The droplets of a sneeze travel as fast as 150 feed a second and as far as 12 feet which has the potential of infecting numerous other persons in a high density area such as an office, subway, train or airplane. Another method of transportation of pathogens is to be carried on the skin, primarily the human hand and be deposited on another persons's hand or on an object which touches the other person.

It is highly desirable to protect people from pathogenic organisms. In those individuals with active respiratory infection, it is also desirable to decrease the likelihood of dissemination of infection by reducing or eliminate disease transmissions through the fingers and hand contact of an infected person.

BACKGROUND OF THE INVENTION

Respiratory infections are the result of the exposure to pathogenic bacteria, viruses, and fungi. The immunological response to infections consists of the neutralization and destruction of the invader by immunoglobulins circulating in the liquid part of the blood (plasma) and phagocytosis from neutrophils, monocytes, and tissue macrophages. When the infection exceeds the effectiveness of the defense mechanism, illness will result.

Good health, and particularly a strong immunological system, is protective against infections. In the current social conditions, one cannot avoid the effects of the inhalation of pathogens, particularly when subjects are in a closed environment (buildings, airplanes, buses, trains, etc.) or are in physical proximity to individuals who have active respiratory infections and are sneezing, coughing, and expelling microdroplets with a high concentration of pathogens.

When considering the application of a disinfectant to a human, it must be recognized that the human capacity for smell is highly developed and easily desensitized which limits the use of a number of disinfectants. Humans have roughly 1000 receptors capable of recognizing some 10,000 distinct odors and over five million smell-sensing cells having neurons with eight or more stringly cilia. Olfactory neurons undergo constant renewals with an average replacement every one to two months. Olfactor receptor cells have bipolar neurons that are located in the olfactory epithelium under the dorsal aspect of the nasal cavity, the septum and part of the superior turbinates in the nose. Turbinates in the nose create airflow patterns that allow volatile compounds to reach the olfactory cells. Olfactory receptors bind odorants and belong to the 2-G-protein-coupled receptor superfamily associated with the adenyl cyclase and phosophoisoniositol signaling. Coding for odor quality and identification may involve the specific temporal sequences of firing that is compound specific. Axons of olfactory bipolar cells traverse through the small holes in the cribiform plate of the ethmoidal bone to the olfactory bulb where they form synapses in intricate masses called glomeruli. There is, thus, a neuroanatomical overlap which provides an anatomical basis for the capacity of odor to produce hedonic responses. Olfactory information is ultimately transmitted to the hypothalamus and this anatomical structure emphasizes the importance of olfaction in eating and nutrition. Thus, it is important when treating disease that these sensor functions are not desensitized or overpowered by the chemical compound being used to treat the infection.

Rubbing alcohol (isopropyl alcohol, isopropanol) does not contain ethyl or grain alcohol and is generally used as a 70.0% mixture with water for rubdowns because it cools the skin by evaporation and causes pore to close. Isopropyl alcohol has been used for sterilizing and preparing needles and syringes for hypodermic injection. It is also used as a solvent for medicine, as a steriliant for instruments and as a skin cleanser before drawing blood or giving injections. Isopropyl alcohol has been shown to be an excellent antiseptic product. It appears to be lethal to bacteria, fungi and viruses, including the AIDS virus.

Isopropyl alcohol of at least 50.0% by weight mixed with sesame oil (40.0% by weight) and lemon oil 1.0% to 3.0% in weight to obtain a mucosal disinfectant for topical application in the nose is disclosed in U.S. Pat. No. 6,296,882 issued Oct. 2, 2001 to the present inventor. However, this solution layers with the oils and alcohol forming separate layers. Isopropyl alcohol has also been effectively used as a solution and as a spray for its antiseptic properties as is shown in U.S. Pat. Nos. 5,145,663 issued Sep. 8, 1992; 5,432,165 issued Jul. 11, 1994 and 5,441,723 issued Aug. 15, 1995.

The present invention is based on the discovery that the present invention has multipurposes in that it is germicidal and has an effectiveness over 8 hours. The solution remains clear and stable over six months without layering and sterilizes the skin, tongue and surfaces of objects which are used or engaged by human beings.

SUMMARY OF THE INVENTION

The non-toxic topical disinfectant comprises a novel composition of isopropyl alcohol, sesame oil, lemon oil, and menthol in specific relative proportions by weight. The non-toxic topical solution may be used safely to disinfect the skin, tongue, and hard surfaces of objects through topical application. The interactive composition comprises at least 24% to 27% by weight of isopropyl alcohol, from about 63% to about 73% by weight sesame oil, from 1.0% to 3.0% by weight lemon oil and menthol ranging from 0.1% to 1.0% in weight. The menthol is dissolved and dispersed throughout.

It is an object of this invention to topically apply a solution of the composition comprising isopropyl alcohol, sesame oil, lemon oil, and menthol to destroy pathogenic bacteria, viruses and fungi which are present on the area of application and to sterilize skin, the tongue and surfaces of objects.

It is another object of the present invention to create a composition that has a shelf life which is stable for more than six months.

It is yet another object of the present invention to create a composition which is clear to the eye and does not layer (doesn't require shaking before applying).

These and other objects, advantages, and novel features of the present invention will become apparent when considered with the teachings contained in the detailed disclosure.

DETAILED DESCRIPTION OF THE PREFERRED EMBODIMENT

Disinfectants and delivery systems have been developed aimed at destroying various pathogenic organisms. The chemical and biological effectiveness of such disinfectants are limited by their chemical and biological effects.

The present invention of this non-toxic germicidal composite solution composition is effective against various pathogenic organisms which include bacteria (i.e., haemophilus influenza, staphylococcus aureus streptococcus pneumoniae, streptococcus pyrogenes, etc), viruses (i.e., adeno 5 virus, corona virus TGEV, rhino virus type 14, etc.) and fungi by topical application to the surface being treated.

The preferred embodiment of the composition comprises isopropyl alcohol (anhydrous USP not less than 99.0% USP) ranging from about 24.0% to 27.0% by weight, sesame oil ranging from about 63.0% to about 73.0% by weight, lemon oil ranging from about 1.0% to 3.0% by weight and menthol ranging from 0.1% to 1.0% by weight. Other testing has shown effective results with a composition having isopropyl alcohol being used in a range of about 24.0% to about 27.0% weight; sesame oil in the range of about 63.0% to 75.0% by weight, lemon oil in a range of about 0.5 to about 2.0% by weight and menthol in a range of about 0.1% to about 1.0% by weight.

The isopropyl alcohol provides the primary bactericidal and virucidal effect (the killing effect of pathogenic organisms) while the sesame oil provides lubrication while also acting as a disinfectant. The dehydrating effect of isopropyl alcohol is also neutralized by its dilution with the sesame oil while the lemon oil which is added to the composition provides lubrication, fragrance and vitamin C. The menthol is a catalytic agent enhancing penetration and providing a pleasant scent to the solution. Menthol additionally provides composition stability and prevents specific gravity layering of the alcohol and oils. The prolonged contact time of the alcohol to the area with microorganisms provides considerable reduction in the number of microorganisms in excess of eight hours.

It can, thus be seen that the non-toxic disinfectant of the subject inventive composition includes four distinct products which actively complement each other. One is the primarily active disinfectant, isopropyl alcohol which is considered to be a safe topical antiseptic to use. Isopropyl alcohol is effective against gram-negative and gram-positive bacteria, fungi, viruses including hepatitis B and C, HIV, RSV, CMV, influenza and the herpes family. Bacterial resistance to isopropyl alcohol is very slight to non-existent.

Sesame Oil, Ben (n) e, Gingelly, Simsin, til or ufuta Oil is the oil extracted from the seeds of Sesamum indicium (Pedalialcae). Sesame Oil as an oily product which has 22.0% total fat, 10.0% of saturated fat, and polyunsaturated and monounsaturated fat and is non-toxic. The best sesame oil and the sesame oil used in the present invention is 100% pure expeller pressed. It is an antibacterial disinfectant for common skin pathogens such as staphylococcus and streptococcus as well as common skin fungi.

Lemon oil is an essential oil meaning conditioning the essence of lemons. It takes 1000 pounds of fresh lemons to make 10 pounds of pure lemon oil. This oil is derived primarily from the rind and skin of the lemon and contains no scents or preservatives. The lemon oil used in the present composition should be 100% pure USP Grade. Lemon oil maintains a balance between oxidation and reduction reactions and captures oxygen and delivers hydrogen inside cells. Quercetin, a component of lemon oil and the aroma of lemon oil absorbed through the olfactory system can restore immune system functioning impaired by stress. The lemon oil adds vitamin C to the infection site which is effective against infections.

Menthol has a natural antibacterial activity and serves to enhance rapid penetration of the other agents on the skin and tongue surfaces as well as the surfaces of inert objects and keeps the composition from layering into specific gravity components. Menthol also has analgesic activity to provide relief from pain or soreness while giving a pleasant scent to the composition.

Isopropyl alcohol, when used by itself, is an irritant, dissipates rapidly and has a strong scent would make it unacceptable.

Alcohol and oil do not interact chemically and the composition must be thoroughly mixed by shaking. When lemon oil is added to these other two ingredients, it contributes to the lubrication of the surface and introduces a scent which makes the combination of substances more agreeable, without harming the sensory receptors. Furthermore, lemon oil has Vitamin C which has well-known beneficial properties, including protection against infections. Addition of menthol keeps the components from layering thus keeping the composition in the desired mixed ratios and producing a more pleasant scent. Preparation of the composition is shown in the following illustrative examples.

EXAMPLE I

The disinfectant properties of the present composition kill bacteria, viruses and fungi without toxic effects or damage when applied to the surface of the tongue of a human. The proportional relationships of the ingredients is isopropyl alcohol, ranging from about 24.0% to about 27.0% by weight; sesame oil, ranging from about 63.0% to about 73.0% by weight, lemon oil 12 drops for each 10 ml of the isopropyl alcohol/sesame oil mixture about 1.5% by weight, and menthol crystals about 0.3 to about 0.5 grams for each 10 ml of the isopropyl alcohol/sesame oil mixture about 0.5% by weight. Menthol essential oils can be substituted in place of the crystals. The components are mixed at an ambient temperature with a standard mixing apparatus and topically applied as follows:

The composition of Example I was topically applied by spray to the tongue of a human subject with a maximum of 1.0 ml sprayed on the tongue. No growth of bacteria occurred 10 minutes later. The composition when stored in a container remained stable for more than 3 months without layering and retained its solution clarity.

EXAMPLE II

The disinfectant properties of the present composition kill bacteria, viruses and fungi without toxic effects or damage when applied to the skin of a human. The proportional relationships of the ingredients is isopropyl alcohol, ranging from about 24.0% to about 27.0% by weight; sesame oil, ranging from 63.0% to about 73.0% by weight, lemon oil 12 drops for each 10 ml of the isopropyl alcohol/sesame oil mixture about 1.5% by weight, and menthol crystals about 0.3 to about 0.5 grams for each 10 ml of the isopropyl alcohol/sesame oil mixture about 0.5% by weight. The components are mixed at an ambient temperature with a standard mixing apparatus and topically applied as follows:

The composition of Example II was topically applied by application of 1–3 ml dispersed on the hand of a human subject. The composition when stored in a container remained stable and in a clear condition for more than 6 months without layering. The skin was sterilized with normal bacteria/virus/fungi destroyed in infected skin.

EXAMPLE III

The disinfectant properties of the present composition kill bacteria, viruses and fungi, occur without toxic effects or damage to the surface of an object. The proportional relationships of the ingredients is isopropyl alcohol, ranging from about 24.0% to about 27.0% by weight; sesame oil, ranging from about 63.0% to about 73.0% by weight, lemon oil 12 drops for each 10 ml of the isopropyl alcohol/sesame oil mixture about 1.5% by weight, and menthol crystals about 0.3 to about 0.5 grams for each 10 ml of the isopropyl alcohol/sesame oil mixture about 0.5% by weight. The components are mixed at an ambient temperature with a standard mixing apparatus and topically applied as follows:

The composition of Example III was topically applied to the tooth brush and dental floss by solution and on the surface of other objects. The composition is a clear solution which remains stable for more than 3 months.

When exposed to an undiluted solution of the test product for one (1) minute, microbial populations of haemophilus influenzae, staphylococcus aureus, streptococcus pneumoniae and streptococcus pyogenes were reduced by 99.9999%. No viable immuno-organisms could be detected within limits of the test.

Effect of Composition on bacteria, virus and fungi:

1. The present inventive composition solution is effective in decreasing bacterial growth to at least a 6.0 $\log_{10}$ reduction when compared to normal bacteria growth.

2. The present inventive composition solution is effective in decreasing virus growth to at least a 2.7 $\log_{10}$ reduction when compared to normal virus growth.

3. The present inventive composition solution is effective in decreasing fungi growth when compared to normal fungi growth.

In the foregoing description, the invention has been described with reference to a particular preferred embodiment, although it is to be understood that specific details as shown are merely illustrative, and the invention may be carried out in other ways without departing from the true spirit and scope of the following claims.

What I claim is:

1. A non-toxic disinfectant composition for topical application to the skin comprising a composition of isopropyl alcohol of at least 24.0% to about 27.0% by weight; sesame oil of at least 53.0% by weight, lemon oil ranging between 1.0% to 2.0% in weight and menthol ranging from about 0.1% to about 1.0% in weight, mixed homogeneously, said sesame oil supplementing and neutralizing the dehydrating effect of the alcohol.

2. A non-toxic disinfectant composition according to claim 1, wherein said sesame oil is about 63.0% to about 67.0% by weight.

3. A non-toxic disinfectant composition according to claim 1, wherein said menthol is present from about 0.3 to about 0.5 grams per each 10 ml mixture of the isopropyl alcohol and sesame oil.

4. A non-toxic disinfectant composition according to claim 1, wherein said composition has an effective treatment life of at least eight hours and is stable for at least six months.

5. A non-toxic disinfectant composition according to claim 1, wherein said composition decreases bacterial growth to at least a 6.0 $\log_{10}$ reduction when compared to normal bacterial growth.

6. A non-toxic disinfectant composition according to claim 1, wherein said composition decreases viral growth to at least a 2.7 $\log_{10}$ reduction when compared to normal viruses growth.

7. A disinfectant composition for topical application to a human comprising a composition of isopropyl alcohol of at least 24.0% by weight; sesame oil ranging from about 63.0% is about 67.0% by weight, lemon oil not exceeding 3.0% by weight and menthol not exceeding 1.0% by weight, mixed homogeneously, said sesame oil supplementing and neutralizing the dehydrating effect of the alcohol and said menthol increasing shelf stability.

8. A disinfectant composition according to claim 7, wherein said composition has an effective treatment life of at least eight hours.

9. A disinfectant composition according to claim 7 wherein said isopropyl alcohol is anhydrous USP which is not less than 99.0% USP.

10. A disinfectant composition according to claim 7 wherein said sesame oil is 100% pure expeller pressed.

11. A disinfectant composition according to claim 7 wherein said lemon oil is 100% pure USP Grade.

12. A disinfectant composition according to claim 7 wherein said composition has a shelf life over 3 months.

13. A disinfectant composition according to claim 7 wherein said composition is a solution which is clear.

14. A non-toxic disinfectant composition according to claim 7, wherein said composition decreases bacterial growth to at least a 6.0 $\log_{10}$ reduction when compared to normal bacterial growth.

15. A non-toxic disinfectant composition according to claim 7, wherein said composition decreases viral growth to at least a 2.7 $\log_{10}$ reduction when compared to normal viruses growth.

16. A disinfectant composition for objects comprising a composition of a solution isopropyl alcohol of about 24.0% to about 27.0% by weight; sesame oil ranging from about 63.0% to about 73.0% by weight, lemon oil ranging between about 0.1% to about 3.0% in weight and menthol ranging from about 0.5% to 1.0% in weight, mixed homogeneously, said sesame oil supplementing and neutralizing the dehydrating effect of the alcohol and said menthol eliminating the layering of the alcohol and oils.

17. A disinfectant composition according to claim 16 wherein said isopropyl alcohol is anhydrous USP which is not less than 99.0% USP.

18. A disinfectant composition according to claim 16 wherein said sesame oil is 100% pure expeller pressed.

19. A disinfectant composition according to claim 16 wherein said lemon oil is 100% pure USP Grade.

20. A disinfectant composition according to claim 16 wherein said composition has a shelf life over 6 months.

21. A disinfectant composition according to claim 16 wherein said composition is a solution which is clear.

22. A dental floss comprising an effective amount of the disinfectant composition of claim 16.

23. A toothbrush comprising an effective amount of the disinfectant composition of claim 16.

* * * * *